US008951464B2

(12) United States Patent
Specht et al.

(10) Patent No.: US 8,951,464 B2
(45) Date of Patent: Feb. 10, 2015

(54) METHOD FOR MANUFACTURING A MEDICAL IMPLANT AND MEDICAL IMPLANT

(75) Inventors: Heiko Specht, Hanau (DE); Andreas Reisinger, Alzenau (DE); Goran Pavlovic, Schaafheim (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 0 days.

(21) Appl. No.: 13/331,516

(22) Filed: Dec. 20, 2011

(65) Prior Publication Data

US 2012/0158110 A1    Jun. 21, 2012

(30) Foreign Application Priority Data

Dec. 20, 2010   (DE) .................. 10 2010 055 175

(51) Int. Cl.
*B22F 7/02* (2006.01)
*B22F 3/10* (2006.01)
*B22F 3/11* (2006.01)
*B22F 3/02* (2006.01)
*B22F 7/00* (2006.01)
*A61N 1/05* (2006.01)

(52) U.S. Cl.
CPC ............ *B22F 3/1109* (2013.01); *B22F 3/02* (2013.01); *B22F 7/002* (2013.01); *A61N 1/056* (2013.01)
USPC ...................................... 419/6; 419/2; 419/7

(58) Field of Classification Search
USPC ................................... 419/2, 6, 7
See application file for complete search history.

(56) References Cited

U.S. PATENT DOCUMENTS

| 2,830,218 | A | * | 4/1958 | Beggs .................. 313/346 DC |
| 4,011,861 | A | | 3/1977 | Enger |
| 4,612,160 | A | | 9/1986 | Donlevy et al. |
| 4,830,822 | A | * | 5/1989 | Ward ........................ 428/547 |
| 5,080,672 | A | * | 1/1992 | Bellis ......................... 427/2.1 |
| 5,097,843 | A | * | 3/1992 | Soukup et al. .............. 607/116 |
| 5,104,410 | A | * | 4/1992 | Chowdhary .............. 623/11.11 |
| 5,853,652 | A | * | 12/1998 | Schildgen et al. .......... 264/614 |
| 7,632,454 | B2 | * | 12/2009 | Schlesser et al. ............. 419/39 |
| 2009/0317278 | A1 | * | 12/2009 | Kokubo ........................ 419/2 |

FOREIGN PATENT DOCUMENTS

| DE | 102008037200 | 2/2010 |
| WO | 2008064672 | 6/2008 |
| WO | 2010017959 | 2/2010 |

* cited by examiner

*Primary Examiner* — George Wyszomierski
*Assistant Examiner* — Ngoclan T Mai
(74) *Attorney, Agent, or Firm* — Dicke, Billig & Czaja, PLLC

(57) ABSTRACT

One aspect relates to a medical implant, for example, implantable stimulation electrode, having a tight substrate and a porous contact region. One aspect also relates to a lead of a cardiac pacemaker having an implantable stimulation electrode and to a method for manufacturing a medical implant, for example, an implantable stimulation electrode.

A medical implant according to one aspect is characterized in that the implant includes a sintered body with graduated porosity.

9 Claims, 3 Drawing Sheets a)

b)

METHOD FOR MANUFACTURING A MEDICAL IMPLANT AND MEDICAL IMPLANT

CROSS-REFERENCE TO RELATED APPLICATIONS

This Utility Patent Application claims priority to German Patent Application No. DE 10 2010 055 175.9, filed on Dec. 20, 2010, which is incorporated herein by reference.

BACKGROUND

One aspect relates to a medical implant, for example, an implantable stimulation electrode, having a tight substrate and a porous contact region. One aspect also relates to a lead of a cardiac pacemaker having an implantable stimulation electrode and to a method for manufacturing a medical implant, for example, an implantable stimulation electrode.

Medical implants of different types generally have to meet multiple requirements. They need to be biocompatible and integrate well into surrounding body tissue. Further requirements depend on the nature and/or type of the medical implant. Accordingly, prostheses, for example articular prostheses, need to have high stability. Implantable stimulation electrodes of cardiac pacemakers for implantation into the heart need to show good electrical conductivity and low impedance in order to transmit stimulatory pulses effectively to the heart tissue to be stimulated without over-straining the battery of the cardiac pacemaker and exhausting it prematurely. They also need to have a low input impedance in order to be sensitive to the electrical signals from the heart that are monitored by the cardiac pacemaker and to whose irregularities or absence the cardiac pacemaker responds through electrical stimulatory pulses.

In order to harmonize the various requirements, articular prostheses sometimes include a stable core regions of which are surrounded by a porous material. This is generated, for example according to U.S. Pat. No. 4,612,160 A, in that a section of a prosthesis with a smooth surface is provided with a layer of sinter particles that are sintered to it. The irregular and porous surface structure generated by this means promotes the integration of the prostheses into a bone through bone tissue growing into the pores.

In the case of implantable stimulation electrodes, it is customary to manufacture a substrate that forms the core of the stimulation electrode from a solid piece of metal by milling or lathing with a machine, for example from platinum or a platinum-iridium alloy (PtIr). Subsequently, a porous structure made of a similar or the same biocompatible material is sintered onto the solid and polished substrate. Said manufacturing process necessitates several individual working steps. This applies, for example, to the manufacturing of the substrate and/or form body onto which the porous structure is subsequently sintered and, if applicable, to the generation of transverse drill holes or longitudinal slits and the de-burring after a lathing step.

The corresponding medical implants and/or implantable stimulation electrodes form the extreme distal end of a lead of a cardiac pacemaker that leads from a body pocket, in which the cardiac pacemaker is accommodated, though a caval vein to the heart. The stimulation electrode is anchored in the cardiac wall through barbed hooks.

Following the implantation of the stimulation electrode in the cardiac wall, a fibrous capsule with a thickness of up to 3 mm may form around the stimulation electrode as a defense reaction, which impairs the electrical coupling of the stimulation electrode to the tissue by increasing the output and input impedance. The formation of said capsule is being reduced, if applicable, through the administration of pertinent active substances.

The porous surface structure of the head of the stimulation electrode, which forms a contact region of the stimulation electrode, also reduces the defense reaction and facilitates the ingrowth of cardiac wall tissue into the pores of the stimulation electrode. This enables good electrical contact both for the application of stimulatory pulses into the cardiac wall and for measurement of electrical fields in the cardiac wall.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The invention is described in the following based on exemplary embodiments and reference being made to the drawings though without limiting the general scope of the invention in any way or form, whereby reference is made expressly to the drawings with regard to all details according to the invention that are not illustrated more closely in the text. In the figures.

DETAILED DESCRIPTION

Figure 1:
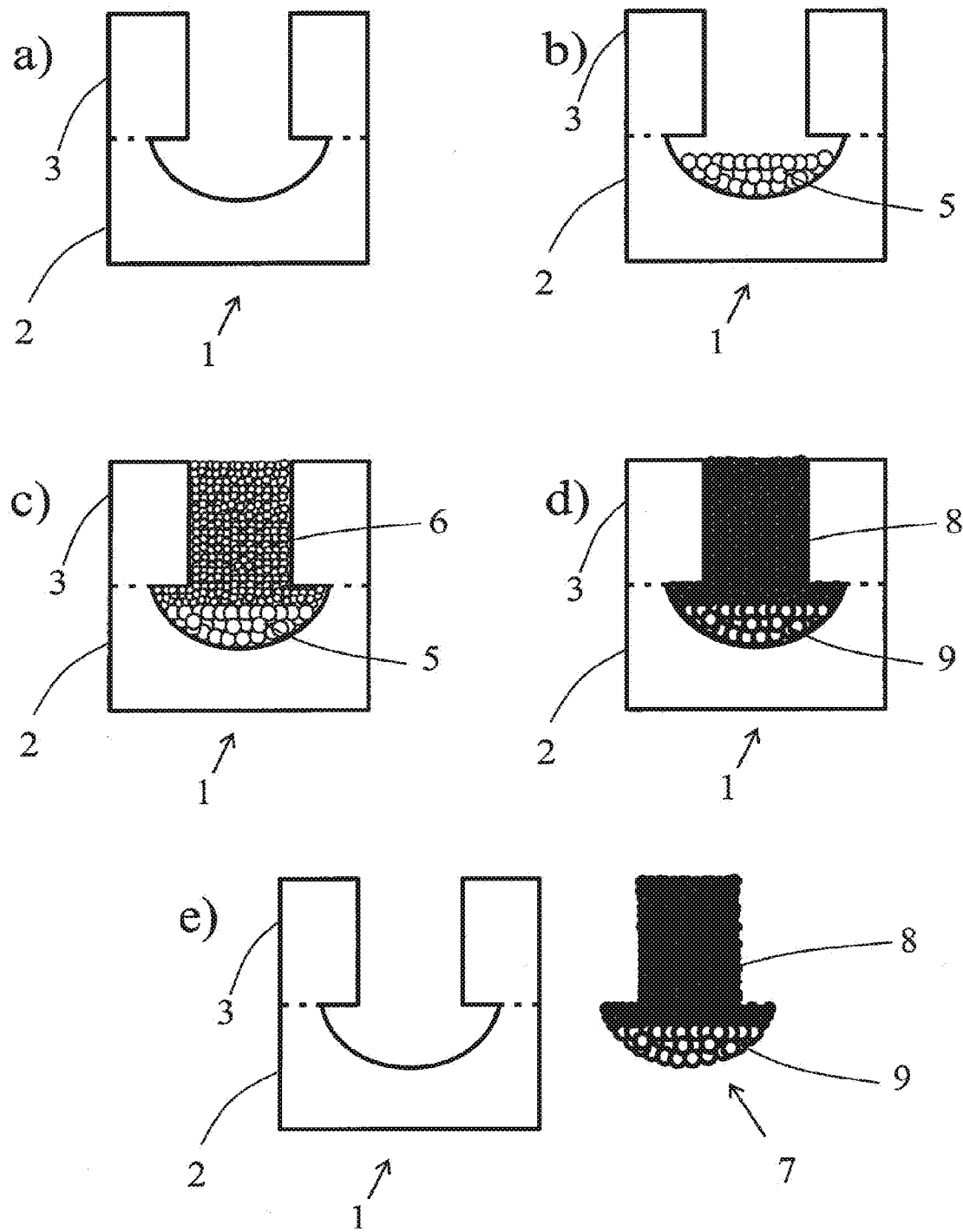
FIG. 1 illustrates a schematic view of a method according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Identical or like elements and/or corresponding parts are identified in the following figures through the same reference numbers such that there is no need to introduce each again in each case.

One embodiment specifies a medical implant that is rapid and inexpensive to manufacture, and specifies a method for manufacturing said implant, for example, with regard to an implantable stimulation electrode.

In one embodiment a medical implant, for example, implantable stimulation electrode, has a tight substrate and a porous contact region that is developed further in that the implant includes a sintered body with graduated porosity.

In one embodiment, a sintered structure is used instead of a combination of a solid form body onto which a porous structure is sintered. Said sintered structure includes graduated porosity with regions of different porosity. An open-pore structure is present, for example, on the head of a stimulation electrode that is provided as contact region for cardiac tissue or on the external surface of an articular implant that is provided as contact region for a bone tissue. A narrow-pore or negligible-pore structure is present in the implant in the region of the substrate that substitutes for the mechanical and/or electrical properties of a lathed solid form body, as used previously, for example of an articular prosthesis or of a substrate of a stimulation electrode.

In the scope of one embodiment, the term, graduated porosity, shall be understood to mean that a firmly bonded, contiguous sintered body has different porosity in various regions. The porosity can change between the regions differing in porosity either incrementally with very small transitional regions or gradually between larger regions. The entire implant can also have a fully gradual profile of porosity without any larger regions with constant porosity.

One embodiment includes both regions with large and open pores and regions with smaller, nearly closed or negligible pores and regions comprising no or only very few completely closed pores owing to intensive sintering, whereby the pore structure is closed to the extent that the individual pores are not connected to each other. The latter structure is also called "tight" in the scope of one embodiment, even if it cannot always be ensured during sintering that all pores vanish. A material of this type that is sintered to be tight has similar mechanical and electrical properties as a lathed solid form body and/or a corresponding substrate.

Since a sinter body with graduated porosity can be sintered in one process, this dispenses with the laborious procedural step of producing and forming or lathing a form body as substrate from a solid material. The shape of the implant is pre-determined through the sinter mold, whereby the mold advantageously is dimensioned such that the shrinkage occurring during the sintering is compensated. Moreover, sintering causes substrate and contact region to be connected in a firmly bonded manner and therefore to be connected very well to each other. The connection is at least as good as the connection of a material sintered onto a smooth surface of a solid form body, since the sinter particles of the contact region and of the substrate have become mixed to some extent, at least over a small space, in a boundary layer.

In the scope of one embodiment, the region of an implant with high porosity is called contact region and a region of low porosity is called substrate. This region is also called head in implantable stimulation electrodes. In articular prostheses for implantation into a bone, this nomenclature calls the external highly porous layer that forms a connection to the bone contact region, whereas the substrate situated on the inside has lower porosity and is essential for the mechanical stability of the implant.

In one embodiment, the contact region includes high porosity having at least a partially patent pore structure and the substrate includes no patent pore structure. Accordingly, the substrate is essentially tight, whereas the contact region improves the ingrowth and/or contacting of tissue.

In one embodiment, the implant is or can be produced through co-sintering two sinter fractions in a sinter mold, whereby the sinter fractions consist of powders or slurries of sinter particles of a conductive material that differ in their average particle size and/or composition of the material with respect to the melting point. This manufacturing method is simple, since a given sinter mold can be filled easily with two different sinter materials in two sinter fractions. These can be either powders or slurries.

In the scope of one embodiment, slurries are suspensions of particles of a powder made of one or more materials in a liquid binding agent, usually in water or in an organic binding agent. A slurry has a high viscosity and can be shaped and dosed easily without applying high pressure. In terms of the dosability, a slurry is advantageous as compared to a powder in that liquids are easier to dose than powders and a slurry shows higher cohesion than a powder and thus the slurries of the first fraction and of the second fraction are easy to separate from each other. Powders allow a gradual porosity profile to be adjusted more easily.

Sintering a slurry, it is important to make sure to first use a relatively flat temperature curve in a relatively low temperature range, in which the binding agent evaporates, in order to give the binding agent time to evaporate gradually without evaporating under formation of shock waves and thus destroying the sinter structure. After complete evaporation of the binding agent, the desired sintering temperature below the melting point of the sinter material or sinter materials used can be established.

During sintering, which is generally carried out below the melting temperature of the materials used, but in individual cases is carried out just above the melting temperature of the lower-melting component of a multi-component mixture, surface diffusion processes and volume diffusion processes cause sintering necks to be formed in the sinter particles between the particles of the powder that effect firmly bonded connection of the particles to each other without necessarily melting the particles completely. Simultaneously, the particles of the material move closer to each other which cause the hollow spaces between the particles to decrease in size. The workpiece shrinks in the process. Said process proceeding in a form body that is sintered to be tight leads to hermetic sealing of the sintered material with respect to gases and liquids.

The sinter particles of the two sinter fractions differ in their size, composition of their material with respect to the melting temperature or both. Both lead to implant regions arising that differ in porosity.

The sinter particles of one embodiment consist of Pt, PtIr, TaNbW, Pd, PdIr, Au, Ti, Nb, TiNb or the sinter particles include said materials. These elements and alloys are materials with good sintering properties that have high biocompatibility.

In one embodiment, the average particle sizes of the first sinter fraction and second sinter fraction differ by a factor of more than 1.5, in one embodiment between 2 and 10, in one embodiment between 5 and 8.

Selecting sinter particles for the first sinter fraction and the second sinter fraction that differ in average particle size has the effect that the distances between the sinter particles of the sinter fraction having the larger particle size at the start of sintering are larger. Accordingly, the hollow spaces between the sinter particles in this fraction are larger. The hollow spaces decrease in size during sintering, but not to the extent to close altogether. Moreover, the surface diffusion processes and volume diffusion processes of large particles do not affect the entire volume of the sinter particles such that these do not melt completely and only form the known sintering necks. As a result, the sinter fraction with the large sinter particles attains an open-pore structure.

In the sinter fraction with the small sinter particles, the hollow spaces between the sinter particles are already markedly smaller than in the other fraction at the start of the sintering process such that the hollow spaces shrink and vanish earlier in the course of the sintering process. Simultaneously, the particles are so small, if applicable, that the surface diffusion process and the volume diffusion process affect the smaller sinter particles completely, if applicable, such that an effect like complete melting is evident. Being positioned closely to each other, the small sinter particles thus form an extensive connection to each other. In other words: the size of the small sinter particles in the second sinter fraction is on the order of magnitude of the sintering necks between them such that the small sinter particles transition completely into the sintering necks and thus into a tight structure.

The sinter part is sintered for as long as necessary to have a structure arise in the fraction with the small sinter particles that is as tight as possible, but only for as long as necessary to have an open-pore structure or an essentially open-pore structure remain in the fraction with the larger sinter particles.

In one embodiment, the average particles sizes of the sinter fractions are in the range between 1 μm and 50 μm. Accordingly, it has proven to be advantageous in one embodiment for the particle sizes of the first sinter fraction, which is, for example, the sinter fraction for the contact region of a stimulation electrode, to be between 30 and 45 μm, and the particle size of the other fraction forming the substrate of the implant to be less than 10 μm.

One variant of independent inventive merit consists of the graduated porosity being generated or being supported in that materials differing in melting temperatures are used, in one embodiment in combination with different particle sizes. Proceeding as described, the effect according to one embodiment of the implant having graduated porosity is based on the sinter temperature employed being closer to the melting point of the low-melting material of the one fraction and farther away from the melting temperature of the higher-melting material of the other sinter fraction. The extent of surface and volume diffusion is higher in the lower-melting material than in the higher melting material such that larger sintering necks are formed in the lower-melting material and the hollow spaces between the sinter particles shrink more rapidly than in the higher-melting material. This can be combined with different particle size in order to either increase or attenuate the effect. The latter is the case, for example, if one sinter fraction includes higher-melting smaller sinter particles and the other sinter fraction includes lower-melting larger sinter particles. By this means, profiles or steps of porosity can be fine-tuned through suitable selection or combination of the features of the sinter particles.

In one embodiment, the melting points of the material employed in the first sinter fraction and of the material employed in the second sinter fraction differ by more than 10° C., and in one embodiment by more than 30° C.

The substrate in one embodiment includes an external thread for a lead onto which the lead can be coiled.

One embodiment is a lead of a cardiac pacemaker having an implantable stimulation electrode as described above, whereby the lead contacts the substrate of the stimulation electrode, for example, through being coiled around it and/or through welding or solder spots.

One embodiment is a method for manufacturing a medical implant, for example, an implantable stimulation electrode, which is provided, as described above, including the procedural steps:

partly filling a sintering mold for the medical implant with a first sinter fraction made of a powder or slurry with sinter particles of an electrically conductive material such that an unoccupied space remains in the sintering mold;

at least partly filling the remaining space of the sintering mold with a second sinter fraction made of a powder or slurry with sinter particles of a conductive material that differ from the sinter particles of the first sinter fraction in their average particle size and/or composition of the material with respect to the melting point;

generating a medical implant with graduated porosity through co-sintering the two sinter fractions in the sintering mold.

Each of the procedural steps described above is significantly simpler and less time-consuming and less expensive than the manufacturing method used thus far, in which a solid form body was lathed as substrate. The shape of the stimulation electrode as well as the porosity and tightness of the contact region and substrate can be controlled well. This also applies to other medical implants, for example implantable articular prostheses.

In order to promote cohesion of the first sinter fraction, an advantageous refinement according to one embodiment provides the first sinter fraction to be pre-sintered or partly sintered in the sintering mold before the remaining space in the sintering mold is filled with the second sintering fraction. In this case, the first sinter fraction can, for example, be the substrate that is joined to each other, before the porous contact region material is filled into the mold as second sinter fraction. And, vice versa, it is just as well to pre-sinter the contact region.

In one embodiment, a part of the implant with high porosity is generated from one sinter fraction and a tight part of the implant with low or negligible porosity is generated from the other sinter fraction. This concerns, for example, the contact region and the substrate of the implant.

The sinter particles of the sinter fractions, in one embodiment, consist of Pt, PtIr, TaNbW, Pd, PdIr, Au, Ti, Nb, TiNb or alloys thereof or include said materials.

It is also preferable, in one embodiment, for the average particle sizes of the first sinter fraction and second sinter fraction to differ by a factor of more than 1.5, in one embodiment, between 2 and 5. In one embodiment, the average particles sizes of the particles of the sinter fractions are in the range between 10 μm and 50 μm.

The melting points of the material used in the first sinter fraction and of the material used in the second fraction, in one embodiment, differ by more than 10° C., in one embodiment, by more than 30° C.

In one embodiment, the sinter mold is dimensioned to be larger than the finished medical implant in its region for the contact region and in the region of the substrate, each according to the different shrinkages of the sinter fractions during the sintering.

The features, properties and advantages specified with regard to the various subject matters of the invention, that is, with regard to the medical implant, lead and method for manufacturing a medical implant, shall also apply, without limitation, to the respective other subject matters of the invention reference to which is expressly made herewith.

FIGS. 1*a*) to 1*e*) schematically illustrate the essential procedural steps of the method according to one embodiment for manufacturing a medical implant, in the present case, an implantable stimulation electrode. In each case, a sintering mold 1 is illustrated as a cross-section and consists of a head mold 2 for the contact region and of a substrate mold 3. The head mold 2 and the substrate mold 3 result in a hollow space that has a mushroom-like structure, whereby the head is wider than the stem. The stem can later be contacted by a lead. The head mold 2 and the substrate mold 3 are separable along a dashed line to allow a finished implant 7 to be taken out of the mold after its manufacture.

FIG. 1*b*) illustrates a first procedural step, in which a powder or slurry of a first sinter fraction 5 having large sinter particles is filled into the head mold 2. Said first sinter fraction 5 shall later form the biocompatible and tissue ingrowth-promoting surface of an implantable stimulation electrode for a cardiac pacemaker. In a second procedural step that is illustrated in FIG. 1*c*), the remaining space in the sintering mold 1 above the first sinter fraction 5 is filled up with a powder or slurry of a second sinter fraction 6. It consists of smaller sinter particles as compared to those of the first sinter fraction 5.

FIG. 1*d*) illustrates that the sinter mold 1 containing the sinter fractions 5 and 6 has meanwhile been sintered. This is illustrated in that the line thickness used for the powder particles has been made thicker and reflects the action of surface diffusion and volume diffusion in the sinter particles during the sintering, which leads to the formation of sintering necks and reduction of the size of the hollow spaces between the sinter particles.

In FIG. 1*d*), all sinter particles in sinter fractions 5 and 6 have been joined to each other through the formation of sintering necks such that the first sinter fraction 5 has been converted into a head 9 and/or contact region and the second sinter fraction 6 has been converted into a substrate 8. The substrate 8 is tight, that is, its pores have either vanished or are not connected to each other such that there is no longer a patent pore structure present in substrate 8. Owing to the particle size, a patent pore structure is still provided in the head 9 even after the sintering.

FIG. 1*e*) illustrates that the stimulation electrode 7 with its tight substrate 8 and porous head 9 has meanwhile been taken out of the sintering mold 1. Substrate 8 and head 9 of the stimulation electrode 7 have also been sintered together such that these two parts of the stimulation electrode 7 are joined firmly to each other.

Figure 2:
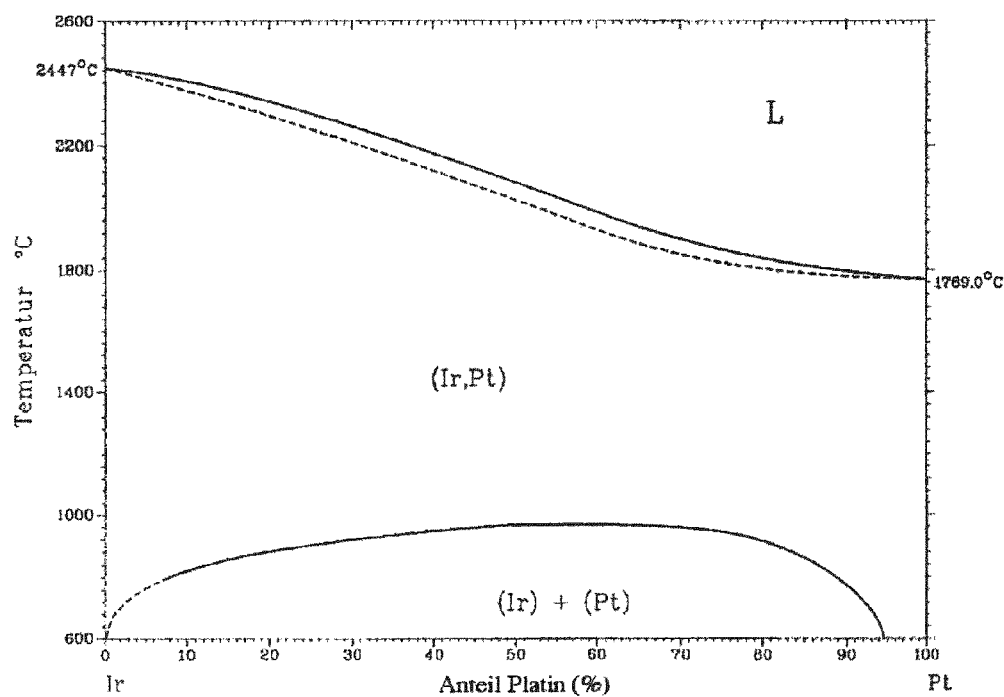
FIG. 2 illustrates a phase diagram of a PT-IR system.

FIG. 2 illustrates a phase diagram of the system made up by iridium and platinum (PtIr). The platinum fraction of said system is illustrated on the horizontal axis. The platinum fraction on the left side is 0%. This corresponds to pure iridium. The platinum content on the right side is 100% meaning pure platinum in this place. A temperature is plotted on the vertical axis in degrees centigrade.

The phase diagram is sub-divided into three regions, whereby the mixture is present in a liquid phase (L, liquid) above the upper continuous line. The upper continuous line is also called liquidus line and identifies the melting temperature of the mixture for different platinum and iridium fractions. For iridium, it ends at the melting point of iridium at approx. 2,447° C., and for platinum, it ends at the melting point of platinum at approx. 1,769° C.

The dashed line below the liquidus line is called solidus line. It separates the phase region in the middle, in which a solid mixture of iridium and platinum (Ir, Pt) exists, from the liquid region (L) above the liquidus line. Since iridium and platinum have different melting points, the concentrations in this boundary region of iridium and platinum in the solid phase (Ir,Pt) differ from that in the liquid phase (L) as platinum has the lower melting point and tends to become enriched in the liquid phase. Accordingly, an equilibrium between the liquid phase (L) and the solid phase (Ir,Pt) exists between two values that are connected to each other on the liquid line and the solidus line by a horizontal line at a given temperature. In this equilibrium state between the two phases, platinum is therefore more enriched in the liquid phase (L) and iridium is more enriched in the solid phase (Ir,Pt).

The lower line in the phase diagram in FIG. 2 separates the phase (Ir,Pt), in which iridium and platinum are present next to each other as a mixture, from a phase region (Ir)+(Pt), in which iridium and platinum segregate or sequester from each other and each form own domains in the material. Said sequestration takes a certain time to complete such that the material should be cooled rapidly in order to keep the sequestration to the smallest extent possible and to thus obtain a homogeneous mixed structure even at low temperatures, for example at a body temperature of 37° C.

It is evident from the phase diagram illustrated in FIG. 2 that the materials in the various sinter fractions in the method according to one embodiment can just as well be materials with different fractions of a mixture made up of the same two components. Accordingly, for example pure platinum on the one hand and a platinum-iridium alloy having an iridium fraction of 10% on the other hand can be used. In this case, the melting points differ according to the liquidus line by 10 to 20° C. At a sintering temperature just below 1,769° C., for example at 1,750° C., the difference from the melting point of platinum is only approx. 20° C., whereas the melting point of the platinum-iridium (10%) alloy is approx. 30 to 40° C. above the sintering temperature. This means that the formation of sintering necks and the reduction of the size of hollow spaces is going to proceed more rapidly in the pure platinum fraction than in the alloy fraction.

Figure 3:
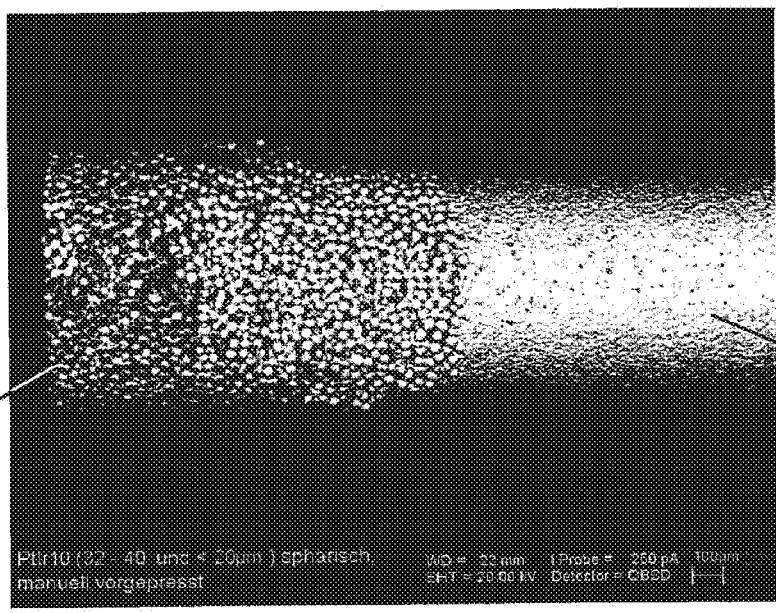
FIG. 3 illustrates micrographs of a form body with graduated porosity.
Figure 3:
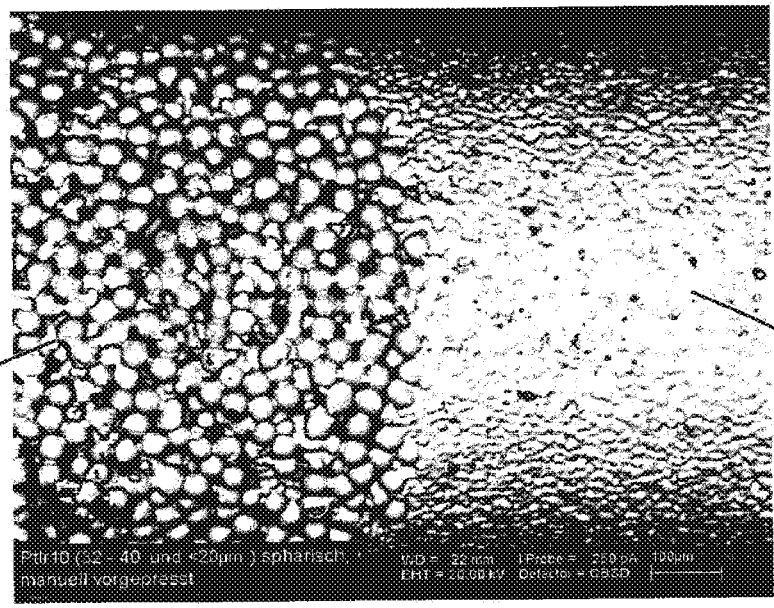

FIG. 3*a*) illustrates an electron micrograph of a sintered form body made of a platinum-iridium alloy having a 10% fraction of iridium as an implementation of the feature of graduated porosity according to one embodiment. A sintered substrate 8 having a tight structure is illustrated on the right side and transitions at a separating surface into a head 9 that has a porous structure. The tight structure of the substrate 8 still includes some hollow spaces, but no permeable pore structure. The sinter particles became connected to each other in this region to a large degree, whereby the majority of the pores has closed completely.

For the manufacture, a part to be sintered was pre-pressed manually, whereby sinter particles with a diameter between 32 μm and 40 μm were used in the head 9 and sinter particles with a diameter of less than 20 μm were used in the substrate 8. A scale is illustrated in the right bottom corner. The bar indicates a length of 100 μm.

FIG. 3*b*) illustrates a magnified detail view of FIG. 3*a*). The magnification is larger than that in FIG. 3*a*) by a factor of approximately 2. The figure illustrates the transition of the substrate 8 into the head 9. A tight structure has formed in the substrate 8 and still contains some hollow spaces, although these are not connected to each other. In a transitional region that is equal to several diameters of the smaller sinter particles, the sinter particles of the fraction of the substrate 8 and the fraction of the head 9 have become mixed with each other. The smaller sinter particles have become arranged between the larger sinter particles in this transitional region.

During the sintering, the larger sinter particles of the head 9 and the smaller sinter particles of the substrate 8 became joined to each other. By this means, a stable, extensive and electrically conductive connection was generated between the two parts.

The workpiece illustrated in FIGS. 3*a*) and 3*b*) is a prototype that was manufactured according to the method according to one embodiment. It is evident from FIG. 3*a*) that the two fractions leading to the substrate 8 and head 9 have shrunk to different degrees during the sintering process. The original mold had a constant diameter. The more extensive elimination of pores in substrate 8 caused this part of the cylinder to shrink more strongly than the head 9. Said differential shrinkage is compensated in that the sintering mold is dimensioned appropriately such that both regions have the desired dimensions after the specific shrinkage process during the sintering occurred.

Electrical contacting of the substrate 8 to a lead wire is effected, for example, through coiling the lead wire, which is generally coiled like a helix, in sections around the substrate 8 and connecting it to the substrate 8 through some welding spots.

All features specified including the features that are evident from the drawings alone as well as individual features that are disclosed in combination with other features, are considered to be essential for the invention both alone and in combination. Embodiments according to the invention can be implemented through individual features or a combination of multiple features.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for manufacturing an implantable stimulation electrode having a tight substrate and a porous contact region, the method comprising:
    partly filling a sintering mold for the implantable stimulation electrode with a first sinter fraction made of a powder or slurry with sinter particles of an electrically conductive material such that an unoccupied space remains in the sintering mold;
    at least partly filling the remaining space of the sintering mold with a second sinter fraction made of a powder or slurry with sinter particles of a conductive material that differ from the sinter particles of the first sinter fraction in their average particle size and/or composition of the material with respect to the melting point;
    generating the implantable stimulation electrode with graduated porosity through co-sintering the two sinter fractions in the sintering mold;
    characterized in that a part of the implant with high porosity is generated from one sinter fraction and a tight part of the implant with low or negligible porosity is generated from the other sinter fraction; and
    characterized in that the melting points of the material employed in the first sinter fraction and of the material employed in the second sinter fraction differ by more than 30° C.

2. The method according to claim 1, characterized in that the sinter particles of the sinter fractions consist of Pt, PtIr, TaNbW, Pd, PdIr, Au, Ti, Nb, TiNb or alloys thereof or comprise said materials.

3. The method according to claim 1, characterized in that the average particle sizes of the first sinter fraction and second sinter fraction differ by a factor of between 2 and 5.

4. The method according to claim 1, characterized in that the average particles sizes of the particles of at least one of the first and second sinter fractions are in the range between 10 μm and 50 μm.

5. The method according to claim 1, characterized in that the sinter mold is dimensioned to be larger than the finished medical implant in the region for the contact region and in the region of the substrate, each according to the different shrinkages of the sinter fractions during the sintering.

6. A method for manufacturing an implantable stimulation electrode having a tight substrate and a porous contact region, the method comprising:
    partly filling a sintering mold for the implantable stimulation electrode with a first sinter fraction made of a powder or slurry with sinter particles of an electrically conductive material such that an unoccupied space remains in the sintering mold;
    at least partly filling the remaining space of the sintering mold with a second sinter fraction made of a powder or slurry with sinter particles of a conductive material that differ from the sinter particles of the first sinter fraction in their average particle size and/or composition of the material with respect to the melting point; and
    generating the implantable stimulation electrode with graduated porosity through co-sintering the two sinter fractions in the sintering mold;
    characterized in that the first sinter fraction is pre-sintered or partly sintered in the sintering mold before the remaining space of the sintering mold is filled with the second sintering fraction; and
    characterized in that the melting points of the material employed in the first sinter fraction and of the material employed in the second sinter fraction differ by more than 30° C.

7. A method for manufacturing an implantable stimulation electrode having a tight substrate and a porous contact region, the method comprising:
    partly filling a sintering mold for the implantable stimulation electrode with a first sinter fraction made of a powder or slurry with sinter particles of an electrically conductive material such that an unoccupied space remains in the sintering mold;
    at least partly filling the remaining space of the sintering mold with a second sinter fraction made of a powder or slurry with sinter particles of a conductive material that differ from the sinter particles of the first sinter fraction in their average particle size and/or composition of the material with respect to the melting point; and
    generating the implantable stimulation electrode with graduated porosity through co-sintering the two sinter fractions in the sintering mold;
    characterized in that the average particle sizes of the first sinter fraction and second sinter fraction differ by a factor of between 5 and 8.

8. A method for manufacturing an implantable stimulation electrode having a tight substrate and a porous contact region, the method comprising:
    providing a sintering mold for the implantable stimulation electrode, the mold having a hollow structure defining a stem and a head, the head being wider than the stem thereby defining a neck therebetween;
    partly filling a portion of the head of the sintering mold with a first sinter fraction made of a powder or slurry with sinter particles of an electrically conductive material such that an unoccupied space remains in the head of the sintering mold after all of the first sinter fraction is added;
    at least partly filling the remaining space of the head and the stem of the sintering mold with a second sinter fraction made of a powder or slurry with sinter particles of a conductive material that differ from the sinter particles of the first sinter fraction in their average particle size and/or composition of the material with respect to the melting point and such that the second sinter fraction fills around the neck; and generating the implantable stimulation electrode with graduated porosity through co-sintering the two sinter fractions in the sintering mold.

9. The method according to claim 8, characterized in that particles of the first and second sinter fractions are in the range between 10 μm and 50 μm.

* * * * *